United States Patent
Vautravers et al.

(10) Patent No.: US 10,961,177 B2
(45) Date of Patent: Mar. 30, 2021

(54) PROCESS FOR PREPARING AN ANTICORROSION COMPONENT FOR AN ANTIFREEZE

(71) Applicant: BASF SE, Ludwigshafen am Rhein (DE)

(72) Inventors: Nicolas Vautravers, Ludwigshafen am Rhein (DE); Joaquim Henrique Teles, Ludwigshafen am Rhein (DE); Henning Althoefer, Ludwigshafen am Rhein (DE); Harald Dietl, Ludwigshafen am Rhein (DE)

(73) Assignee: BASF SE

( * ) Notice: Subject to any disclaimer, the term of this patent is extended or adjusted under 35 U.S.C. 154(b) by 0 days.

(21) Appl. No.: 16/494,970

(22) PCT Filed: Mar. 6, 2018

(86) PCT No.: PCT/EP2018/055443
§ 371 (c)(1),
(2) Date: Sep. 17, 2019

(87) PCT Pub. No.: WO2018/172062
PCT Pub. Date: Sep. 27, 2018

(65) Prior Publication Data
US 2020/0283365 A1    Sep. 10, 2020

(30) Foreign Application Priority Data
Mar. 21, 2017    (EP) ..................... 17161965

(51) Int. Cl.
C07C 51/235    (2006.01)
C09K 5/20    (2006.01)
C23F 11/12    (2006.01)

(52) U.S. Cl.
CPC .............. *C07C 51/235* (2013.01); *C09K 5/20* (2013.01); *C23F 11/126* (2013.01)

(58) Field of Classification Search
CPC ........ C07C 51/235; C23F 11/126; C09K 5/20
See application file for complete search history.

(56) References Cited

U.S. PATENT DOCUMENTS

| | | | |
|---|---|---|---|
| 4,238,625 A | 12/1980 | Fiege et al. | |
| 4,256,916 A * | 3/1981 | Morris .................. | C07C 51/235 562/537 |
| 4,524,969 A | 6/1985 | Erzmoneit | |
| 4,561,990 A | 12/1985 | Darden | |
| 10,202,324 B2 | 2/2019 | Vautravers et al. | |
| 10,259,822 B2 | 4/2019 | Werner et al. | |
| 10,487,194 B2 | 4/2019 | Werner et al. | |
| 10,385,033 B2 | 8/2019 | Gordillo et al. | |
| 10,435,381 B2 | 10/2019 | Teles et al. | |
| 2018/0290959 A1 | 10/2018 | Thrun et al. | |
| 2018/0312458 A1 | 11/2018 | Thrun et al. | |
| 2018/0362351 A1 | 12/2018 | Parvulescu et al. | |
| 2018/0362353 A1 | 12/2018 | Vautravers et al. | |
| 2019/0004005 A1 | 1/2019 | Oja et al. | |
| 2019/0077779 A1 | 3/2019 | Riedel et al. | |
| 2019/0177260 A1 | 6/2019 | Vautravers et al. | |
| 2019/0202778 A1 | 7/2019 | Thrun et al. | |
| 2019/0210989 A1 | 7/2019 | Teles et al. | |

(Continued)

FOREIGN PATENT DOCUMENTS

| | | |
|---|---|---|
| DE | 2936123 A1 | 4/1981 |
| DE | 3135946 A1 | 3/1983 |
| DE | 3135846 A1 | 4/1983 |

(Continued)

OTHER PUBLICATIONS

Chemical Abstracts Servie: Columbus, OH, US; Zhang, Y., et al., "Preparation of Diglycolic Acid via Oxidation of Diethylene Glycol with Molecular Oxygen", XP002781224, retrieved from Scientific & Technical Information Network, Database Accession No. 2012:1169993.

(Continued)

*Primary Examiner* — Paul A Zucker
(74) *Attorney, Agent, or Firm* — Faegre Drinker Biddle & Reath LLP

(57) ABSTRACT

A process for preparing an anticorrosion component for an antifreeze by oxidizing an oxydiol of the formula (I)

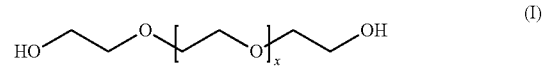

with molecular oxygen at a temperature of 20 to 100° C. and a partial oxygen pressure of 0.01 to 2 MPa in the presence of water and of a heterogeneous catalyst. The catalyst contains platinum to form an oxydicarboxylic acid of the formula (II)

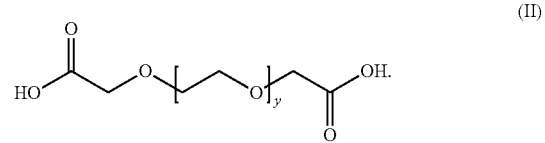

The process has the steps of conducting the oxidation
(a) at a molar ratio of $0.002 \leq n(\text{Pt})/[n(\text{oxydiol (I)})+n(\text{oxydicarboxylic acid (II)})] \leq 0.019$;

(b) at a concentration of water of 50% to 95% by weight in the liquid phase; and
(c) at a pH of 1 to 7.

14 Claims, No Drawings

(56) References Cited

U.S. PATENT DOCUMENTS

| | | |
|---|---|---|
| 2019/0322634 A1 | 10/2019 | Teles et al. |
| 2019/0330171 A1 | 10/2019 | Parvulescu et al. |

FOREIGN PATENT DOCUMENTS

| | | |
|---|---|---|
| EP | 0229440 B1 | 6/1990 |
| EP | 0479470 B1 | 5/1995 |
| EP | 0552988 B1 | 10/1995 |
| WO | WO-2017207461 A1 | 12/2017 |

OTHER PUBLICATIONS

Ein-Eli, Y., "Enhanced Corrosion Inhibition of Zn in Alkaline Solutions Containing Poly(ethylene glycol) Diacid", Electrochemical and Solid-State Letters, vol. 7, No. 1, (2004), pp. B5-B7.

International Search Report for PCT/EP2018/055443 dated Jun. 5, 2018.

Written Opinion of the International Searching Authority for PCT/EP2018/055443 dated Jun. 5, 2018.

Zhang, Y., et al., "Preparation of Diglycolic Acid via Oxidation of Diethylene Glycol with Molecular Oxygen", Fine Chemicals, vol. 29, No. 5, published by Jingxi Huagong Bianjibu, (2012), pp. 517-520 (English translation from Chinese).

U.S. Appl. No. 16/311,198, filed Dec. 19, 2018.
U.S. Appl. No. 16/461,134, filed May 15, 2019.
U.S. Appl. No. 16/461,696, filed May 16, 2019.
U.S. Appl. No. 16/462,430, filed May 20, 2019.
U.S. Appl. No. 16/470,834, filed Jun. 18, 2019.
U.S. Appl. No. 16/494,910, filed Sep. 17, 2019.

Donze, C., et al., "Aerobic selective oxidation of (hetero)aromatic primary alcohols to aldehydes or carboxylic acids over carbon supported platinum", Applied Catalysis B: Environmental, vol. 70, Issue 1-4, Jan. 31, 2007, pp. 621-629.

Fiege, H., et al., "Activation of Oxidations with Oxygen on Platinum Metals Using the Example of the Conversion of 2-Phenoxyethanols to Phenoxyacetic Acids", Angewandte Chemie International edition, vol. 20, Issue 9, Sep. 1981, pp. 783-784.

Heyns, K., et al., "Katalytische oxydation von primären and sekundären hydroxylverbindungen mit sauerstoff am platinkontakt in flüssiger phase : Über katalytische cxydationen—XIV", Tetrahedron, vol. 9, Issues 1-2, 1960, pp. 67-75.

\* cited by examiner

PROCESS FOR PREPARING AN ANTICORROSION COMPONENT FOR AN ANTIFREEZE

CROSS-REFERENCE TO RELATED APPLICATIONS

This application is a national stage application (under 35 U.S.C. § 371) of PCT/EP2018/055443, filed Mar. 6, 2018, which claims benefit of European Application No. 17161965.3, filed Mar. 21, 2017, both of which are incorporated herein by reference in their entirety.

The present invention relates to a process for preparing an anticorrosion component for an antifreeze by oxidizing an oxydiol of the general formula (I)

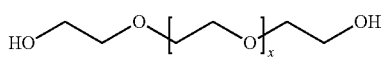

in which x is 0 (zero) or a positive integer from 1 to 10 with molecular oxygen at a temperature of 20 to 100° C. and a partial oxygen pressure of 0.01 to 2 MPa in the presence of water and of a heterogeneous catalyst comprising platinum to form an oxydicarboxylic acid of the general formula (II)

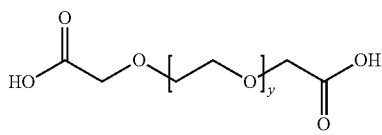

in which y is 0 (zero) or a positive integer from 1 to 10.

Antifreezes are used particularly in cooling circuits of internal combustion engines in order to prevent freezing of the cooling fluid therein at low temperatures. The antifreeze is added in the required amount to the actual cooling medium, which is generally water.

The main constituent of the antifreezes is typically low molecular weight alkylene glycols such as ethylene glycol and propylene glycol. At the same time, antifreezes are also intended to protect the cooling circuit from corrosion. Therefore, anticorrosives are generally added to the antifreezes. These are usually a mixture of different substances from various chemical substance classes. An important substance class among the anticorrosives used is that of mid- to long-chain carboxylic acids. These are typically saturated and unsaturated, branched and unbranched, aliphatic and aromatic mono- and dicarboxylic acids having usually 3 to 16 carbon atoms.

EP 0,479,470 B1 discloses an antifreeze composition in which, as well as further components, neopentanoic acid, isononanoic acid, neoheptanoic acid, dimethylglutaric acid, diethylmalonic acid, 2-ethylbutyric acid, methyvaleric acid, suberic acid, azelaic acid, sebacic acid, undecanedioic acid, dodecanedloic acid, dicyclopentadienedioic acid or terephthalic acid are used as anticorrosive. Sebacic acid (decanedioic acid) is mentioned as being particularly suitable.

EP 0,552,988 B1 describes an antifreeze composition in which, as well as further components, malonic acid, succinic acid, glutaric acid, adipic acid, pimelic acid, sebacic acid, azelaic acid, itaconic acid or hexanoic acid are used as anticorrosive. Sebacic acid and azelaic acid (nonanedioic acid) are mentioned as being particularly preferred.

U.S. Pat. No. 4,561,990 teaches, as anticorrosive, the use of a mixture of an alkali metal molybdate and a $C_{8-12}$-dicarboxylic acid such as suberic acid, azelaic acid, sebacic acid, undecanedioic acid or dodecanedioic acid, with emphasis here too on sebacic acid as being particularly preferred.

EP 0,229,440 B1 mentions an antifreeze composition in which, as well as further components, octanoic acid, nonanoic acid, decanoic acid, undecanoic acid, dodecanoic acid, suberic acid, azelaic acid, sebacic acid, undecanedloic acid, dodecanedioic acid, dicyclopentadienedioic acid or terephthalic acid are used as anticorrosive. Sebacic acid was mentioned with particular preference in this enumeration as well.

Although the mono- and dicarboxylic acids mentioned in the prior art cited above have a good anticorrosive effect, they are in some cases preparable in greater volumes only with difficulty owing to their chemical structure. Moreover, the long-chain mono- and dicarboxylic acids in particular show low solubility in polar media such as water. For example, sebacic acid in water at 20° C. has only a solubility of about 1 g/L.

In the course of the search for an improved antifreeze and anticorrosive, a concentrate having improved properties has now been found. This comprises
(1) 1% to 10% by weight of a mixture of

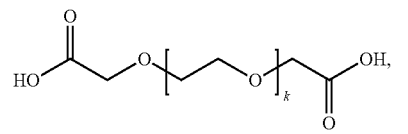

30-100% by weight of

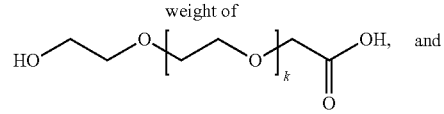

0-40% by weight of

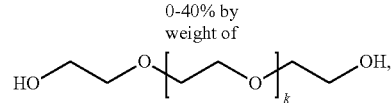

0-30% by weight of

where k is in each case independently 0 (zero) or a positive integer from 1 to 10, and the sum total of the amounts of the three components is 100% by weight, and
(2) 90% to 99% by weight of further components.

The further components mentioned may be additives from one or more substance classes. These may, for example, be monohydric, dihydric or trihydric alcohols, polyhydric alcohols or ethers thereof. Examples of such alcohols include ethylene glycol, 1,2-propylene glycol (propane-1,2-diol), diethylene glycol, dipropylene glycol, triethylene glycol, tetraethylene glycol, pentaethylene glycol, hexaethylene glycol, dipropylene glycol, tripropylene glycol, tetrapropylene glycol, pentapropylene glycol, hexapropylene glycol, 1,3-propylene glycol, glycerol, monoethers of glycols such as the methyl, ethyl, propyl and butyl ethers of ethylene glycol, propylene glycol, diethylene glycol and dipropylene glycol. Preference is given to ethylene glycol, propylene glycol and glycerol, especially ethylene glycol.

Further possible additives in the concentrate include
(a) aliphatic, cycloaliphatic or aromatic monocarboxylic acids each having 3 to 16 carbon atoms in the form of their alkali metal, ammonium or substituted ammonium salts;
(b) aliphatic or aromatic di- or tricarboxylic acids each having 3 to 21 carbon atoms in the form of their alkali metal, ammonium or substituted ammonium salts;
(c) alkali metal borates, alkali metal phosphates, alkali metal silicates, alkali metal nitrides, alkali metal or alkaline earth metal nitrates, alkali metal molybdates or alkali metal or alkaline earth metal fluorides;
(d) aliphatic, cycloaiphatic or aromatic amines which have 2 to 15 carbon atoms and may additionally comprise ether oxygen atoms or hydroxyl groups;
(e) mono- or polycyclic, unsaturated or partly unsaturated heterocycles which have 4 to 10 carbon atoms and may be benzofused and/or may bear additional functional groups;
(f) tetra($C_1$-$C_8$-alkoxy)silanes (tetra-$C_1$-$C_8$-alkyl orthosilicates);
(g) carboxamides or sulfonamides;
(h) hard water stabilizers based on polyacrylic acid, polymaleic acid, acrylic acid-maleic acid copolymers, polyvinylpyrrolidone, polyvinylimidazole, vinylpyrrolidone-vinylimidazole copolymers and/or copolymers of unsaturated carboxylic acids and olefins.

For production of a ready-to-use antifreeze, the concentrate found should be diluted with a base antifreeze which then constitutes the main constituent of the ready-to-use antifreeze. As mentioned at the outset, in the present case too, the base antifreeze used is in particular low molecular weight alkylene glycols such as ethylene glycol and propylene glycol.

An essential component of the anticorrosion concentrate found is the oxydicarboxylic acid

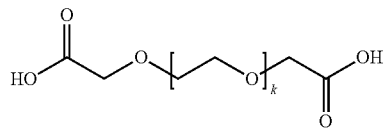

in which k is as defined above. Oxydicarboxylic acids can be prepared, for example, by oxidizing the —$CH_2OH$ groups of the corresponding oxydiols. The corresponding oxydiols are obtainable relatively easily on the industrial scale by polymerizing ethylene oxide in the presence of water or by ethoxylating ethylene glycol with ethylene oxide.

A standard method for oxidation of —$CH_2OH$ groups to the corresponding —COOH groups is heterogeneously catalyzed oxidation with oxygen in aqueous liquid phase in the presence of a Pt-containing catalyst. For instance, K. Heyns at al., Tetrahedron, 1960, vol. 9, 67-75 examines the Pt-catalyzed oxidation of primary and secondary hydroxyl compounds to the corresponding aldehydes, ketones and carboxylic acids. It was found therein that, in neutral solution, primary alcohols are oxidized essentially solely to the aldehydes and the small amounts of acid that are formed by partial further oxidation of the aldehydes inhibit further oxidation, and so the yields are low. Only by addition of at least stoichiometric amounts of alkali, for example NaOH, was it possible to achieve good yields of carboxylic acids.

C. Donze et al., Applied Catalysis B: Environmental 70 (2007) 621-629 confirms this finding using the example of the Pt-catalyzed oxidation of benzyl alcohol. Without addition of NaOH, even after several hours of reaction time, only small amounts of benzoic acid were obtained, whereas the selectivity for benzaldehyde was very high. Only in the presence of an at least stoichiometric amount of NaOH was it possible to obtain the benzoic acid in high yield.

H. Fiege et al., Angew. Chem. 93 (1981) no. 9, 812-813 and U.S. Pat. No. 4,238,625 show that, even in the presence of an at least stoichiometric amount of NaOH over a catalyst with 1% Pt on activated carbon, there is no oxidation of 2-aryloxyethanol. Only by provision of a Pt-containing catalyst activated by Pb, Bi and/or Cd was oxidation to give 2-aryloxyacetic acids enabled.

DE 31 35 946 A1 teaches the oxidation of 2-alkyloxyethanols in an aqueous alkaline medium with oxygen in the presence of a Pt-containing catalyst activated with Pb, Bi and/or Cd to give the corresponding 2-alkyloxyacetic acids. This document too shows, through control experiments, that, even in the presence of an at least stoichiometric amount of NaOH, over a non-Pb-, -Bi- and/or -Cd-activated catalyst with 1% Pt on activated carbon, there is no oxidation of the 2-alkyloxyethanol. Only by provision of a Pt-containing catalyst activated by Pb, Bi and/or Cd was oxidation to give 2-alkyloxyacetic acid enabled. For the provision of an aqueous alkaline medium, suitable alkalis mentioned are alkaline compounds of alkali metals and alkaline earth metals, for example hydroxides and carbonates of Na and K. Since these are bound stoichiometrically by the alkyloxyacetic acid formed, according to the teaching of DE 31 35 846 A1, they should be used in an excess in an amount of 1 to 1.5 mol of alkali per mole of alkyloxyethanol.

A disadvantage of the abovementioned oxidation processes in the presence of an aqueous alkaline medium is the formation of the corresponding carboxylic salt as a direct oxidation product. The free carboxylic acid is obtainable therefrom only in a subsequent step by reaction with an acid and isolation from the acidified solution. This procedure is not just very complex but additionally entails at least stoichiometric use of a base and subsequently at least stoichiometric use of an acid. Thus, an at least stoichiometric amount of salt is produced, which has to be removed and disposed of.

DE 29 36 123 A recognized, at least for the oxidation of 2-alkyloxyethanols, that oxidation over Pt-containing catalysts leads to formation of 2-alkyloxyacetic acids even without addition of a base. For instance, in example 1, the oxidation of methylglycol over 5% Pt on activated carbon at a molar ratio of Pt to methylglycol of 0.0065 and a reaction temperature of 45° C. at standard pressure achieved a yield of methoxyacetic acid of 95%. However, in the oxidation of higher molecular weight alkoxyacetic acids, such as n-butylglycol and methyldiglycol, in spite of a higher molar ratio of Pt to the corresponding 2-alkyloxyethanol of 0.01 under otherwise identical reaction conditions, distinctly lower yields were obtained than in the case of low molecular weight methylglycol. For instance, the yield of n-butoxyacetic acid was only 90% and that of methoxyethoxyacetic acid only 91%.

U.S. Pat. No. 4,256,916 teaches the oxidation of polyethylene glycol with oxygen in the liquid phase without the addition of a base and in the presence of platinum on activated carbon in a fixed bed reactor to give the corresponding polyethylene glycol diacids, wherein the polyethylene glycol-containing reactant solution flows over the fixed bed catalyst at a rate of 0.1 to 0.6 feet per second (3.05 to 18.3 cm/s). In each of the examples, an aqueous solution of the diethylene glycol or triethylene glycol was introduced into a tubular reactor with a Pt/activated carbon fixed bed catalyst and pumped in circulation with continuous supply of oxygen, such that the flow rate over the catalyst was in the range from 0.1 to 0.4 feet per second (3.05 to 12.2 cm/s). The initial molar ratio of Pt to the polyethylene glycol used (diethylene glycol or triethylene glycol) was in the range from 0.02 to 0.031.

Although the establishment of a high flow rate over the fixed bed catalyst achieved a polyethylene glycol conversion of up to 99%, the yield of the corresponding polyethylene glycol acid was only 49% to 90.7%. Thus, a not inconsiderable portion of the reactant was converted to unwanted by-products. The main by-product was glycolic acid (hydroxyacetic acid). Glycolic acid forms via oxidative degradation of —CH$_2$—O—CH$_2$CH$_2$OH groups. The reaction equation using the example of diethylene glycol is:

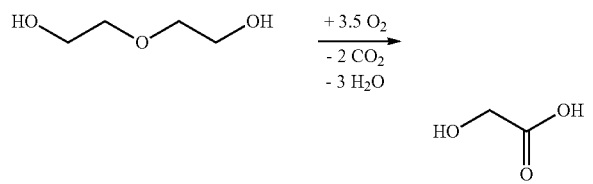

In the examples of U.S. Pat. No. 4,256,916, glycolic acid was obtained in a very high yield of 2.9 to 11.7 g/100 g of diglycolic acid.

The oxidative degradation to glycolic acid not only reduces the yield of the desired diglycolic acid but also leads to loss of valuable CH$_2$ units.

In the context of the present invention, it has been recognized that glycolic acid, being a relatively strong and short-chain acid having a pKa of 3.83, is more likely to promote than reduce corrosion and hence is unsuitable as a constituent in an antifreeze and anticorrosive in an amount as formed by the method of U.S. Pat. No. 4,256,916. If, therefore, one wished to use an oxydicarboxylic acid (polyglycol diacid) prepared by the process of U.S. Pat. No. 4,256,916 as anticorrosion component for an antifreeze, prior removal of the majority of the glycolic acid would be required. However, removal of the glycolic acid from an aqueous polyglycol diacid mixture is extremely difficult. In an attempted distillative separation, as well as the glycolic acid, relatively large amounts of water would inevitably also be removed. This leads not only to distinctly elevated energy expenditure, but also to precipitation of the dewatered polyglycol diacid mixture in the column bottom in solid form owing to the high melting point. In order to keep the polyglycol diacid mixture in the column bottom in liquid form, it would be necessary to constantly add water, which would drive the energy expenditure even higher. Therefore, removal of the glycolic acid from the aqueous polyglycol diacid mixture is economically unviable owing to the extremely poor energy balance. Thus, the process described in U.S. Pat. No. 4,256,916, in spite of use of polyethylene glycol as a readily available feedstock, is unusable for the production of the desired antifreeze and anticorrosive concentrate.

It was therefore an object of the present invention to find a process for preparing an oxydicarboxylic acid suitable for use as anticorrosion component for an antifreeze, which is based on the use of a readily available feedstock, is easy to conduct, enables a high yield and purity, and in particular produces a reaction product usable as anticorrosion component for an antifreeze even without complex purification. In this connection, the reaction product is to comprise only a minor amount, if any, of components that oppose the effect as anticorrosion component for antifreeze. Explicitly, therefore, the content of glycolic acid is to be relatively low.

Surprisingly, a process for preparing an anticorrosion component for an antifreeze by oxidizing an oxydiol of the general formula (I)

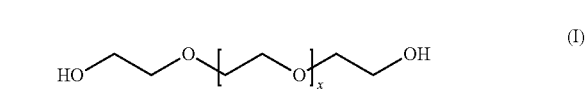

in which x is 0 (zero) or a positive integer from 1 to 10 with molecular oxygen at a temperature of 20 to 100° C. and a partial oxygen pressure of 0.01 to 2 MPa in the presence of water and of a heterogeneous catalyst comprising platinum to form an oxydicarboxylic acid of the general formula (II)

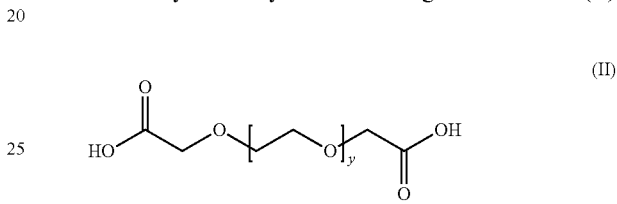

in which y is 0 (zero) or a positive integer from 1 to 10 has been found, in which the oxidation is conducted
(a) at a molar ratio of $$0.002 \leq n(\text{Pt})/[n(\text{oxydiol (I)}) + n(\text{oxydicarboxylic acid (II)})] \leq 0.019$$

where "n(Pt)" is the molar amount of platinum, "n(oxydiol (I))" is the molar amount of oxydiol (I) and "n(oxydicarboxylic acid (II))" is the molar amount of oxydicarboxylic acid (II);
(b) at a concentration of water of 50% to 95% by weight in the liquid phase; and
(c) at a pH of 1 to 7.

The starting material for the preparation of the anticorrosion component mentioned is an oxydiol of the general formula (I)

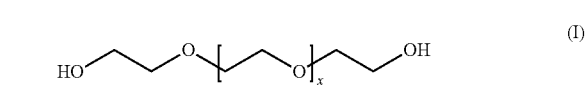

in which x is 0 (zero) or a positive integer from 1 to 10. Preferably, x is a positive integer from 1 to 8, more preferably from 1 to 6, even more preferably from 1 to 5 and especially preferably from 1 to 4.

As already mentioned at the outset, oxydiols (I) are obtainable relatively easily on the industrial scale by polymerizing ethylene oxide in the presence of water or by ethoxylating ethylene glycol with ethylene oxide. Oxydiols (I) having an average molar mass of 200 to 400 g/mol are liquid at room temperature. Since they are hygroscopic, they often comprise small amounts of water.

The oxydiol (I) to be used may be a specific species having a particular value of x or a mixture of oxydiols (I) having different values of x. Since oxydiols (I), as a result of the preparation, are already obtained in the form of mixtures of various oxydiols (I) having different values of x, preference is also given to using corresponding mixtures having different values of x. In practice, these are often identified by the letter combination "PEG" for polyethylene glycol, followed by a number that states the average molar mass. For example, "PEG 200" represents polyethylene glycol having an average molar mass of 200 g/mol.

Thus, preference is given to using a mixture of oxydiols (I) having an average molar mass of 125 to 500 g/mol, more preferably of ≥140 g/mol and even more preferably of ≥150 g/mol, and more preferably of ≤400 g/mol and more preferably of ≤300 g/mol. The average molar mass of the oxydiol (I) is defined as the quotient of the sum total of the masses of the various oxydiols (I) in the mixture and the sum of the molar amount of the various oxydiols (I) in the mixture. The average molar mass can be determined experimentally via measurement of the hydroxyl number, from which the average molar amount of the oxydiols (I) in the mixture can be calculated.

The reactant to be used in the process of the invention may, as well as the oxydiol (I), also comprise further components, for example water. In general, the oxydiols (I), as a result of the preparation, however, are of relatively high purity.

The oxydiol (I) in the process of the invention is oxidized to the oxydicarboxylic acid of the general formula (II)

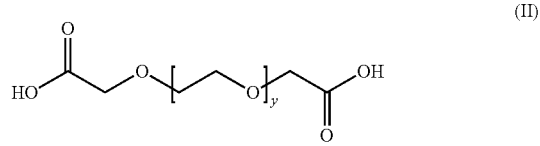

(II)

where y is likewise 0 (zero) or a positive integer from 1 to 10. Preferably, y is a positive integer from 1 to 8, more preferably from 1 to 6, even more preferably from 1 to 5 and especially preferably from 1 to 4.

Like the oxydiol (I) used, the oxydicarboxylic acid (II) formed may also be a specific species or a mixture of various oxydicarboxylic acids (II). If a mixture of various oxydiols (I) is used, a mixture of various oxydicarboxylic acids (II) is also obtained.

The process of the invention is conducted in the presence of water. Water promotes the conversion of the oxydiol (I) to the oxydicarboxylic acid (II) in various ways. For instance, water, in the case of use of a suspension catalyst, improves the suspension thereof in the reaction mixture and additionally also lowers the viscosity of the reaction mixture. The dilution effect reduces the input of heat via the heat of oxidation released and hence counteracts excessive heating. However, the main advantage resulting from the use of water lies in the physical nature of the oxydicarboxylic acids (II). Since these have a distinctly higher boiling point than the corresponding oxydiols (I), in the absence of water, these would precipitate out in solid form in the course of the oxidation reaction and hence prevent a reliable reaction regime with high conversion, high selectivity and easy workup of the reaction mixture. For instance, diglycolic acid (oxydicarboxylic acid (II) with x=0) already has a boiling point above 140° C. On account of the very good solubility in water, the oxydicarboxylic acids formed are kept in solution.

The process of the invention therefore proceeds in aqueous solution in the liquid phase, where the concentration of water in the liquid phase is 50% to 95% by weight. The concentration of water in the liquid phase is preferably ≥60% by weight, and preferably ≤70% by weight.

The catalyst used in the process of the invention is a heterogeneous catalyst comprising platinum as active component. Typically, the platinum is fixed on a support. A wide variety of different materials may be used as support. Examples include inorganic oxides, for instance aluminum oxide, zirconium oxide, titanium dioxide, silicon oxide, inorganic silicates, for instance aluminum silicate, or charcoal. It is of course also possible to use mixtures of different support materials. Preference is given to use of charcoal as support.

The catalyst comprises generally 0.1% to 10% by weight, preferably ≥0.5% by weight, more preferably ≥1% by weight and even more preferably ≥4% by weight, and preferably ≤8% by weight and more preferably ≤6% by weight, of platinum, based in each case on the total mass of the heterogeneous catalyst.

More preferably, in the process of the invention, a heterogeneous catalyst comprising 0.1% to 10% by weight, even more preferably comprising 1% to 10% by weight and especially comprising 4% to 10% by weight of platinum on charcoal is used.

The catalyst to be used may also comprise further metals as well as platinum. The term "further metals" is understood to mean metals from the fourth to sixth periods of groups 3 to 16 of the Periodic Table of the Elements, beginning with scandium (atomic number 21) and ending with polonium (atomic number 84). If further metals are present, the content thereof is advantageously very low. Preferably, the total content of further metals is 0% to 5% by weight, preferably 0% to 1% by weight, more preferably 0% to 0.5% by weight, even more preferably 0% to 0.1% by weight and especially 0% to 0.01% by weight, based on the mass of platinum. In particular, the total content of cadmium, lead and bismuth is preferably 0% to 1% by weight, more preferably 0% to 0.5% by weight, especially preferably 0% to 0.1% by weight, even more preferably 0% to 0.05% by weight and especially 0% to 0.01% by weight, based on the mass of platinum. 1493070DEEN The catalyst is thus preferably prepared without deliberate addition of further metals.

The heterogeneous supported catalyst can be used in various geometric shapes and sizes, for instance as powder or shaped bodies. Pulverulent catalysts may be operated, for example, in suspension mode. In the case of a fixed bed mode, preference is given to using shaped bodies, for example pellets, cylinders, hollow cylinders, spheres or extrudates. The shaped bodies in that case are typically fixed in the reactor by the known methods. In the case of shaped catalyst bodies, these preferably have an average particle size of 1 to 10 mm.

However, preference is given to using the catalyst in the form of a powder. In that case, the pulverulent catalyst is in suspension in the reactor. In order to prevent discharge from the reaction system, a filter is typically used here to retain the suspension catalyst. One example of a customarily used filter is the crossflow filter.

Irrespective of the geometric shape and size of the catalyst particles, the platinum is generally in the form of particles having an average diameter of 0.1 to 50 nm, measured via x-ray diffraction. However, there may also be smaller or larger particles.

In the production of the heterogeneous supported catalyst, the platinum is generally applied to the support by suitable methods.

Platinum is typically applied to the support from solutions of suitable salts. Suitable platinum salts are, for example, those which are soluble in aqueous or aqueous acidic media and from which a platinum compound can be precipitated by an increase in the pH. Preferred examples of a suitable platinum salt include platinum(II) nitrate, platinum(IV) chloride and hexachloroplatinic acid hexahydrate. Useful pH-increasing media especially include aqueous solutions of alkaline salts, for example alkali metal carbonates, preferably sodium carbonate.

For application of the insoluble or sparingly soluble platinum compounds, a wide variety of different methods are possible in principle. In a preferred embodiment, the support is initially charged in a suitable apparatus, for example a rotating drum or a stirred vessel, in supernatant liquid, for example water, and admixed with the solution of the platinum salt and the pH-increasing solution. It is possible here first to add the platinum salt and then the pH-increasing solution, or first a pH-increasing solution and then the platinum salt, or both alternately or else simultaneously.

Preferably, the support is initially charged in water and the pH is increased with the pH-Increasing solution to a value at which the platinum salt precipitates out as an insoluble or sparingly soluble platinum compound. Subsequently, while mixing, the solution of the platinum salt is added, in the course of which the pH is kept, by further addition of the pH-increasing solution, within a range in which the platinum salt precipitates out as an insoluble or sparingly soluble platinum compound. The weight ratio between the total amount of liquid to be added and the support is generally at a value from 1 to 100.

On completion of precipitation, the support comprising the platinum compound is isolated, dried and reduced. Reducing agents used are generally the agents suitable for reduction of precious metal salts. Examples include hydrogen, alcohols, for instance ethanol or isopropanol, and ascorbic acid.

In the impregnation, the solution of a suitable platinum salt is sprayed onto the support in a suitable apparatus, for example a rotating mixing drum. The total amount of platinum salt solution to be sprayed on is preferably at or below the liquid absorption of the initially charged support. In the impregnation, preference is given to using platinum salts that are converted to elemental platinum without residue by heat treatment. Preferred platinum salts for impregnation are, for example, platinum(II) nitrate and hexachloroplatinic acid.

The heterogeneous supported catalyst generally has a BET surface area of $\geq 1$ m$^2$/g and $\leq 10\,000$ m$^2$/g, determined to DIN ISO 9277:2014-01. When carbon is used as support, the BET surface area is preferably in the range of $\geq 500$ m$^2$/g and $\leq 10\,000$ m$^2$/g.

It has now been found that, surprisingly, the amount of platinum used in the oxidation exerts a crucial effect on the amount of glycolic acid formed. When a large amount of platinum is used in relation to the total amount of oxydiol (I) and oxydicarboxylic acid (II) present, a disproportionately large amount of unwanted glycolic acid is formed. As the amount of platinum falls, there is also a fall in the content of glycolic acid in the reaction product, while the reaction rate to give the oxydicarboxylic acid (II) remains sufficiently high over a wide range. Only at a very small amount of platinum does the reaction rate fall to an unattractively low value.

Even more surprising is the finding that the yield of oxydicarboxylic acid (II) distinctly increases as the amount of platinum falls. The exact opposite would actually have been expected. For example, an increase in the amount of platinum to just 40% of the starting value achieved an increase in the yield of oxydicarboxylic acid (II) by around 65% and hence to 165% of the starting value.

Thus, surprisingly, a range for the ratio of the molar amount of platinum based on the sum total of the molar amounts of oxydiol (I) and oxydicarboxylic acid (II) has been found, in which the reaction rate on the one hand is still within an efficient range and the amount of glycolic acid formed on the other hand is sufficiently low that it need not be removed from the reaction mixture in a complex manner when it is used as intended as anticorrosion component. The molar ratio of the invention is $$0.002 \leq n(\text{Pt})/[n(\text{oxydiol (I)}) + n(\text{oxydicarboxylic acid (II)})] \leq 0.019$$

where "n(Pt)" is the molar amount of platinum, "n(oxydiol (I))" is the molar amount of oxydiol (I) and "n(oxydicarboxylic acid (II))" is the molar amount of oxydicarboxylic acid (II). Said molar ratio is preferably $\geq 0.005$ and more preferably $\geq 0.007$, and preferably $\leq 0.017$ and more preferably $\leq 0.015$.

In this connection, however, it should also be mentioned that, as well as the intended oxidation of the —CH$_2$OH groups to the corresponding —COOH groups, according to the reaction scheme shown

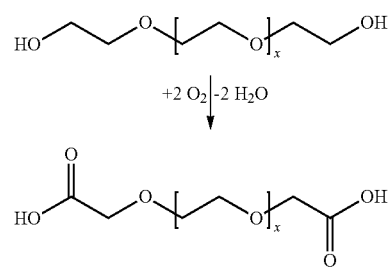

where x is 0 (zero) or a positive integer from 1 to 10, oxidative degradation of —CH$_2$CH$_2$O-groups also takes place to a small degree. For oxydiol (I) with x=1 to 10, the illustrative reaction equation for oxidative degradation is shown below.

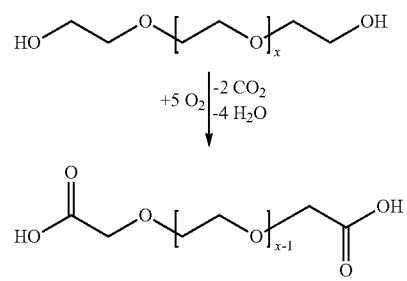

The illustrative reaction equation for the formation of glycolic acid proceeds from oxydiol (I) with x=0.

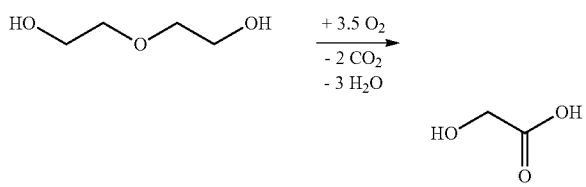

As a result of the oxidative degradation that takes place to a small degree, in the process of the invention, the average chain length decreases somewhat, and so is somewhat smaller than that in the oxydicarboxylic acid (II) obtained than that in the oxydiol (I) used. However, the decrease in the average chain length mentioned is significantly smaller than that in a process above the inventive ratio for the molar amount of platinum based on the sum total of the molar amounts of oxydiol (I) and oxydicarboxylic acid (II).

The high yield of oxydicarboxylic acid (II) with simultaneously very low formation of glycolic acid is achieved in the process of the invention without addition of basic compounds. Correspondingly, the oxidation is conducted at a pH from 1 to 7. Since the feedstock oxydiol (I) is pH-neutral in aqueous solution, the pH on commencement of the oxidation is typically at or close to 7. As a result of the formation of the oxydicarboxylic acid (II), there is a gradual fall in the pH, and so there is generally a value of 1 or 2 toward the end of the oxidation.

As a result of the absence of basic compounds, there is direct formation of the desired oxydicarboxylic acid (II) and not its salt. This has the enormous advantage that the desired oxydicarboxylic acid (II) need not first be released by addition of a stoichiometric amount of extraneous acid. Overall, this saves (i) the use of additional chemicals (base and extraneous acid), (ii) a subsequent workup step including isolation of the oxydicarboxylic acid (II), and (iii) the disposal of the salt formed from the base and the extraneous acid.

The oxidation medium used in the process of the invention is molecular oxygen. Oxygen is added either in pure form or diluted with other gases, for example in the form of air or an $O_2/N_2$ mixture. In order to keep the amount of oxygen to be used as small as possible at a given partial oxygen pressure, the use of a gas with a maximum oxygen content is advantageous. Preferably, therefore, an oxygen is gas having a content of a 90% by volume, more preferably of a 95% by volume, even more preferably of a 99% by volume and especially of ≥99.5% by volume is used. The use of very highly concentrated or pure oxygen makes it possible to keep the amount of offgas relatively small.

In order to promote the distribution of the oxygen in the reactor, it may be advantageous to meter it in in the form of fine bubbles, for example through a frit.

The partial oxygen pressure present in the oxidation is 0.01 to 2 MPa, preferably ≥0.02 MPa and more preferably ≥0.05 MPa, and preferably ≤1 MPa and more preferably ≤0.3 MPa.

The oxidation is effected at a temperature of 20 to 100° C., preferably a ≥30° C. and more preferably ≥40° C., and preferably ≤80° C. and more preferably ≤70° C.

Suitable reactors for performance of the process of the invention are in principle all reactors suitable for the performance of exothermic gas/liquid reactions. Examples include stirred tanks, trickle bed reactors and bubble column reactors. In order to remove the heat of reaction, the reactors are typically equipped with a cooling device. According to the reactor type and nature of the catalyst, the cooling device advantageously comprises cooling elements within the reactor or cooling elements in an external circuit outside the reactor. For example, a stirred tank preferably comprises internal cooling elements, whereas it is more advantageous in a bubble column, for example, to integrate the cooling elements in the external circuit.

If the catalyst is in the form of a shaped body, this is typically fixed in the reactor in the form of a fixed bed. For this purpose, the trickle bed reactor is a particularly useful option, in which the catalyst can be introduced in the form of a bed. But it is possible to use shaped catalyst bodies in a stirred tank reactor. In this case, it is then advantageous to fix the shaped catalyst bodies in a compartment, for example a wire basket.

In the case of the preferred use of a pulverulent catalyst, it is advantageously in suspended form in the reaction mixture. Preferred reactors for the purpose are, for example, stirred tanks or bubble columns. In order to prevent the pulverulent catalyst from settling out, corresponding mixing of the liquid reaction mixture is required. In a stirred tank, this is typically achieved by use of a stirrer. In the case of a bubble column, the mixing is usually achieved via an external circuit with a conveying pump. In principle, the bubble column, with regard to the liquid circuit, can be operated either in upward direction or in downward direction, but operation in downward direction is typically more advantageous.

In the process of the invention, either semicontinuous or continuous operation is possible. In both cases, the oxygen, for assurance of the desired partial pressure, is fed to the reactor continuously or at least intermittently, but preferably continuously.

In the semicontinuous mode of operation, prior to commencement of the reaction, the reactor is initially charged with the complete amount of aqueous reactant mixture together with catalyst and, during the oxidation reaction, no fresh reactant is supplied, nor is any liquid reaction mixture withdrawn. The reactor is not emptied until after the oxidation reaction has ended.

In the continuous mode of operation, there is likewise liquid reaction mixture together with catalyst present in the reactor, but there is constant withdrawal of a small amount of liquid reaction and supply of corresponding amount of aqueous reactant. If a suspension catalyst has been used here, the liquid reaction mixture is advantageously removed from the reactor via a filter device, for example a crossflow filter.

In the process of the invention, it is of course desirable to achieve a maximum conversion of oxydiol (I). Since the reaction rate is defined essentially by the temperature, the partial oxygen pressure and the nature of the heterogeneous catalyst, the desired conversion is ultimately achieved via the reaction time under the defined boundary conditions. Preference is given to choosing a reaction time that enables a conversion of oxydiol (I) of 90% to 100%, more preferably of 95% to 100%, even more preferably of 99% to 100% and especially of 99.9% to 100%. Typically, the reaction time for attainment of a conversion of oxydiol (I) of 90% to 100% is 10 to 60 hours. The reaction time required in the specific individual case is advantageously ascertained either by preliminary experiments under the corresponding reaction conditions or by the recording of suitable measurements during the reaction. Suitable measurements include physical or chemical analyses of the reaction mixture currently present or the amount of oxygen consumed. Physical analyses can be conducted, for example, offline by sampling or online in the reactor or in an external circuit. Possible physical methods include gas chromatography and the measurement of electrical conductivity, of the dielectric constant or of impedance. In the case of measurement of the amount of oxygen consumed, the amount of oxygen supplied is generally employed.

After the end of the reaction, the reaction mixture is typically removed from the reactor and separated from the catalyst. In the case of use of a suspension catalyst, the removal is sensibly by filtration. Alternatively, it is also possible to allow the suspension catalyst to settle out at the reactor base after the end of the reaction and to remove the supernatant liquid. The catalyst removed can generally be reused without further workup.

The reaction mixture obtainable by the process of the invention is notable for a relatively low content of unwanted glycolic acid. It is typically only 0% to 1% by weight, preferably ≥0.1% by weight and more preferably ≥0.2% by weight, and preferably ≤0.7% by weight and more preferably ≤0.5% by weight, based on the oxydicarboxylic acid (II).

Since the reaction mixture separated from the catalyst comprises a considerable portion of water, prior to use thereof as anticorrosion component for an antifreeze, it is advantageous to remove at least some of the water. The simplest technical means in this case is distillative removal since the boiling point of water is well below the boiling points of the oxydicarboxylic acids (II). Therefore, it is preferable in the process of the invention to distillatively remove water from the reaction mixture obtained. Advantageously, the distillative removal of water is conducted under reduced pressure, preferably at a pressure of 0.001 to 0.01 MPa abs.

The reaction mixture worked up by distillative removal of water preferably has a water content of 0% to 40% by weight, preferably of ≥1% by weight and more preferably of ≥2% by weight, and preferably of ≤30% by weight, more preferably of ≤20% by weight and most preferably of ≤10% by weight.

The oxydicarboxylic acid (II) prepared by the process of the invention can be used in an excellent manner as anticorrosion component for an antifreeze.

In a general embodiment of the process of the invention, the desired amount of oxydiol (I) is initially charged in a stirred tank together with the desired amount of pulverulent Pt/activated carbon catalyst, and the contents are brought to the desired reaction temperature while stirring. Then, with further stirring, the introduction of oxygen is commenced and the desired total pressure is established via a pressure-retaining means. The progression of the oxidation is determined in the simplest case from the amount of oxygen metered in. On attainment of the desired conversion, the supply of oxygen is stopped, the mixture is cooled down and decompressed, and the reaction mixture obtained is removed with removal of the catalyst by filtration. The reaction mixture that has been freed of the catalyst is then, in a preferred variant, freed from the majority of the water present.

The mixture processed in this way can then be used without any problem as anticorrosion component for an antifreeze. In the further formulation, it is then possible to mix in the further anticorrosion and antifreeze components.

The process of the invention enables the production of an oxydicarboxylic acid suitable for use as anticorrosion component for an antifreeze in high yield and purity. The oxydiol to be used as feedstock is easy to prepare on the industrial scale and hence also available in relatively large volumes. It is a further feature of the process of the invention that the content of glycolic acid in the reaction product is relatively low and hence there is no need for a complex purification. By simple dewatering under reduced pressure, it is possible to obtain a product mixture with a low water content.

EXAMPLES

Gas Chromatography Analysis

The oxydiol (I) used in the examples and the reaction product obtained were each analyzed by gas chromatography for their organic components. The procedure for this purpose was as follows:

Gas chromatograph: Agilent 7890B

Column: Rxi-1ms (length 30 m, 0.25 mm (ID), 0.25 μm (film)

Temperature program: 3 minutes at 60° C., heating from 60° C. to 290° C. at 5° C./min, 12 minutes at 290° C.

Sample preparation: The catalyst was filtered off and the water was removed. 50 mg of the anhydrous mixture were then mixed with 1 mL of MSTFA (N-methyl-N-(trimethylsilyl)trifluoroacetamide) and heated to 80° C. for 1 hour, and the sample was injected into the gas chromatograph.

Example 1 (Comparative Example)

200 g of pulverulent catalyst having 5% by weight of platinum on activated carbon, corresponding to 10 g or 0.0513 mol of Pt (source: Sigma-Aldrich), were charged into a 4 liter glass reactor and stirred together with 957 g of water at 1000 rpm. Subsequently, 410 g of oxydiol (I) with the distribution shown in table 1a and an average molar mass of 200 g/mol were added, the mixture was equilibrated to 60° C., and 50 L/h of oxygen were passed through the reaction mixture with further stirring. The molar ratio of Pt to oxydiol (I) was thus 0.025, and the concentration of water in the liquid phase was 70% by weight. Since no base had been added, the initial pH was 6.9. After 27 hours, full conversion had been attained. The feed of oxygen was ended, and the reaction mixture was cooled down and discharged from the glass reactor. The reaction mixture had a pH of 1.5. It was filtered through a D4 glass freight and the filtercake was washed three times with 200 mL each time of warm water. The filtrate was then concentrated on a rotary evaporator at 45° C. at a pressure down to 10 mbar. 280 g of product mixture with the composition shown in table 1b were obtained. The analyses of the organic components were each effected by gas chromatography. The water content was determined by Karl Fischer titration.

TABLE 1a

| (reactant) | | | | | | | | |
|---|---|---|---|---|---|---|---|---|
| Oxydiol (I) | x = 0 | x = 1 | x = 2 | x = 3 | x = 4 | x = 5 | x = 6 | x = 7 |
| GC area % | 4.9 | 23.9 | 31.0 | 22.1 | 11.2 | 4.5 | 1.4 | 0.3 |

TABLE 1b

| (product) | | | | | |
|---|---|---|---|---|---|
|  | y = 0 | y = 1 | y = 2 | y = 3 | y = 4 |
| Oxydicarboxylic acid (II) [GC area %] | 26.6 | 31.1 | 24.7 | 11.2 | 1.9 |
| Glycolic acid [GC area %] |  |  | 4.5 |  |  |
| Water [% by wt.] |  |  | 7 |  |  |

Taking account of the water content of 7% by weight and with the approximate estimate that the 4.5 GC area % of glycolic acid corresponds to about 4.5% by weight of glycolic acid based on the anhydrous product mixture, a yield of about 249 g of oxydicarboxylic acid (II) was thus found.

Example 2 (Inventive)

78 g of pulverulent catalyst of the same type as in example 1, having 5% by weight of platinum on activated carbon, corresponding to 3.9 g or 0.020 mol of Pt (source: SigmaAldrich), were charged into a 4 liter glass reactor and stirred together with 957 g of water at 1000 rpm. Subsequently, analogously to example 1, 410 g of oxydiol (I) with the distribution shown in table 1a and an average molar mass of 200 g/mol were added, the mixture was equilibrated to 60° C., and 50 L/h of oxygen were passed through the reaction mixture with further stirring. The molar ratio of Pt to oxydiol (I) was thus 0.0098, and the concentration of water in the liquid phase was 70% by weight. Since no base had been added, the initial pH was 6.9. After 67 hours, full conversion had been attained. The feed of oxygen was ended, and the reaction mixture was cooled down and discharged from the glass reactor. The reaction mixture likewise had a pH of 1.5. It was filtered through a D4 glass freight and the filtercake was washed three times with 200 mL each time of warm water. The filtrate was then concentrated on a rotary evaporator at 45° C. at a pressure down to 10 mbar. 436 g of product mixture with the composition shown in table 2b were obtained. The analyses of the organic components were each effected by gas chromatography. The water content was determined by Karl Fischer titration.

TABLE 2b

| | (product) | | | | |
|---|---|---|---|---|---|
| | $y = 0$ | $y = 1$ | $y = 2$ | $y = 3$ | $y = 4$ |
| Oxydicarboxylic acid (II) [GC area %] | 12.3 | 29.2 | 32.5 | 19.6 | 5.8 |
| Glycolic acid [GC area %] | | | 0.3 | | |
| Water [% by wt.] | | | 4.9 | | |

Taking account of the water content of 4.9% by weight and with the approximate estimate that the 0.3 GC area % of glycolic acid corresponds to about 0.3% by weight of glycolic acid based on the anhydrous product mixture, a yield of about 413 g of oxydicarboxylic acid (II) was thus found.

The two examples show that, in the case of an inventive molar ratio of Pt to oxydiol (I) of 0.0098 (example 2), about a 65% higher yield of oxydicarboxylic acid (II) is obtained than in the case of a molar ratio of 0.025 (example 1). Moreover, at the inventive molar ratio of example 2, only an extremely small amount of 0.3 GC area % of troublesome glycolic acid was formed, whereas, at the higher ratio in example 1, the amount of glycolic acid obtained was 15 times higher at 4.5 GC area %.

Example 3

The catalyst removed in example 2 was used again under the experimental conditions described in example 2. 464 g of product mixture with the composition shown in table 3b were obtained.

TABLE 3b

| | (product) | | | | |
|---|---|---|---|---|---|
| | $y = 0$ | $y = 1$ | $y=2$ | $y = 3$ | $y = 4$ |
| Oxydicarboxylic acid (II) [GC area %] | 11.0 | 29.0 | 33.0 | 20.0 | 6.0 |
| Glycolic acid [GC area %] | | | 0.8 | | |
| Water [% by wt.] | | | 6.8 | | |

Taking account of the water content of 6.8% by weight and with the approximate estimate that the 0.8 GC area % of glycolic acid corresponds to about 0.8% by weight of glycolic acid based on the anhydrous product mixture, a yield of about 429 g of oxydicarboxylic acid (II) was thus found.

Example 4

The catalyst removed in example 3 was used again under the experimental conditions described in example 2. 467 g of product mixture with the composition shown in table 4b were obtained.

TABLE 4b

| | (product) | | | | |
|---|---|---|---|---|---|
| | $y = 0$ | $y = 1$ | $y = 2$ | $y = 3$ | $y = 4$ |
| Oxydicarboxylic acid (II) [GC area %] | 11.1 | 28.5 | 33.0 | 20.5 | 6.3 |
| Glycolic acid [GC area %] | | | 0.7 | | |
| Water [% by wt.] | | | 7.3 | | |

Taking account of the water content of 7.3% by weight and with the approximate estimate that the 0.7 GC area % of glycolic acid corresponds to about 0.7% by weight of glycolic acid based on the anhydrous product mixture, a yield of about 428 g of oxydicarboxylic acid (II) was thus found.

Examples 3 and 4 show that the catalyst used can be reused repeatedly.

The invention claimed is:

1. A process for preparing an anticorrosion component for an antifreeze by oxidizing an oxydiol or a mixture of oxydiols of the general formula (I)

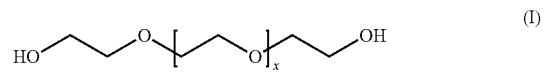

(I)

in which x is a positive integer from 1 to 10 with molecular oxygen at a temperature of 20 to 100° C. and a partial oxygen pressure of 0.01 to 2 MPa in the presence of water and of a heterogeneous catalyst comprising platinum to form an oxydicarboxylic acid of the general formula (II)

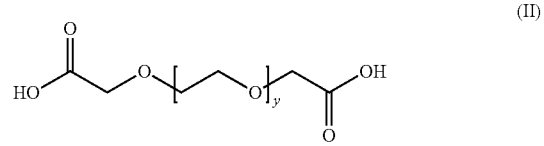

(II)

in which y is a positive integer from 1 to 10, which comprises conducting the oxidation
(a) at a molar ratio of $$0.002 \leq n(Pt)/[n(\text{oxydiol (I)}) + n(\text{oxydicarboxylic acid (II)})] \leq 0.019;$$

where "n(Pt)" is the molar amount of platinum, "n(oxydiol (I))" is the molar amount of oxydiol (I) and "n(oxydicarboxylic acid (II))" is the molar amount of oxydicarboxylic acid (II);
(b) at a concentration of water of 50% to 95% by weight in the liquid phase; and
(c) at a pH of 1 to 7.

2. The process according to claim 1, wherein he oxydiol (I) in which x is a positive integer from 1 to 5 is used.

3. The process according to claim 1, wherein the mixture of oxydiols (I) having an average molar mass of 150 to 300 g/mol is used.

4. The process according to claim 1, wherein a heterogeneous catalyst comprising 0.1% to 10% by weight of platinum on charcoal is used.

5. The process according to claim 1, wherein a heterogeneous catalyst having a total content of cadmium, lead and bismuth of 0% to 0.1% by weight, based on the amount of platinum, is used.

6. The process according to claim 1, wherein the process is conducted at a molar ratio of $$0.005 \leq n(Pt)/[n(\text{oxydiol (I)}) + n(\text{oxydicarboxylic acid (II)})] \leq 0.015;$$

7. The process according to claim 1, wherein a reaction mixture having a content of glycolic acid of 0% to 1% by weight, based on the oxydicarboxylic acid (II), is obtained.

8. The process according to claim 1, wherein water is removed by distillation from the reaction mixture obtained.

9. The process according to claim 8, wherein a processed reaction mixture having a water content of 0% by weight to 40% by weight is produced.

10. The process according to claim 1, wherein the process is conducted at a molar ratio of $$0.007 \leq n(Pt)/[n(\text{oxydiol (I)}) + n(\text{oxydicarboxylic acid (II)})] \leq 0.015;$$

11. The process according to claim 1, wherein the process is conducted at a molar ratio of $$0.005 \leq n(Pt)/[n(\text{oxydiol (I)}) + n(\text{oxydicarboxylic acid (II)})] \leq 0.017;$$

12. The process according to claim 1, wherein the process is conducted at a molar ratio of $$0.007 \leq n(Pt)/[n(\text{oxydiol (I)}) + n(\text{oxydicarboxylic acid (II)})] \leq 0.017;$$

13. The process according to claim 1, wherein the mixture of oxydiols (I) having an average molar mass of 125 to 500 g/mol is used.

14. The process according to claim 1, wherein the mixture of oxydiols (I) having an average molar mass of 140 to 400 g/mol is used.

* * * * *